United States Patent
Loan et al.

(10) Patent No.: US 10,151,674 B2
(45) Date of Patent: Dec. 11, 2018

(54) OIL-BASED MUD DRILL CUTTING CLEANING FOR INFRARED SPECTROSCOPY

(71) Applicant: Schlumberger Technology Corporation, Sugar Land, TX (US)

(72) Inventors: Mary Ellen Loan, Quincy, MA (US); Michael Herron, Ridgefield, CT (US); Ridvan Akkurt, London (GB); Andrew Emil Pomerantz, Lexington, MA (US)

(73) Assignee: SCHLUMBERGER TECHNOLOGY CORPORATION

( * ) Notice: Subject to any disclaimer, the term of this patent is extended or adjusted under 35 U.S.C. 154(b) by 0 days.

(21) Appl. No.: 15/410,045

(22) Filed: Jan. 19, 2017

(65) Prior Publication Data
US 2018/0202906 A1 Jul. 19, 2018

(51) Int. Cl.
*G01N 1/34* (2006.01)
*G01N 21/3577* (2014.01)
*G01N 1/28* (2006.01)

(52) U.S. Cl.
CPC ............ *G01N 1/34* (2013.01); *G01N 1/286* (2013.01); *G01N 21/3577* (2013.01); *G01N 2001/2866* (2013.01)

(58) Field of Classification Search
CPC .......... G01N 1/34; G01N 1/286; G01N 21/35; G01N 21/3577; G01N 2001/2866; G01N 21/3563; E21B 49/00; E21B 49/005
See application file for complete search history.

(56) References Cited

U.S. PATENT DOCUMENTS

| | | | | |
|---|---|---|---|---|
| 4,434,028 A | * | 2/1984 | Eppig | B01D 11/0203 196/14.52 |
| 4,979,393 A | * | 12/1990 | Leung | E21B 49/005 324/376 |
| 5,755,892 A | * | 5/1998 | Herold | B03B 9/02 134/19 |
| 2002/0000399 A1 | * | 1/2002 | Winkler | B01D 29/012 209/399 |
| 2002/0079251 A1 | * | 6/2002 | Schulte | B01D 29/012 209/314 |
| 2010/0250142 A1 | * | 9/2010 | Zamora | E21B 49/08 702/12 |
| 2011/0162441 A1 | * | 7/2011 | Martin | G01N 21/78 73/64.56 |
| 2013/0269420 A1 | * | 10/2013 | Valenza, II | G01N 15/088 73/38 |
| 2013/0269933 A1 | * | 10/2013 | Pomerantz | E21B 21/066 166/264 |
| 2013/0270011 A1 | * | 10/2013 | Akkurt | E21B 49/088 175/58 |
| 2014/0102480 A1 | * | 4/2014 | Pomerantz | B08B 3/10 134/18 |

(Continued)

*Primary Examiner* — Wyatt Stoffa

(57) ABSTRACT

Oil-based mud cuttings are cleaned of drilling fluid and mud additives. After sorting and rinsing the cuttings with diesel, the cuttings are put in a syringe, which is repeatedly filled and emptied of diesel. The cuttings are then washed in the syringe with pentane. The cuttings are then crushed and exposed to a solvent a second time. Instead of placing the cuttings in the syringe, alternatively, the cuttings remain on a sieve and the syringe is used to spray the cuttings with diesel, followed by pentane.

15 Claims, 6 Drawing Sheets

(56) References Cited

U.S. PATENT DOCUMENTS

2014/0369889 A1\* 12/2014 Mostowfi ........... G01N 33/2823
                                                    422/82.09
2015/0136961 A1\*  5/2015 Eddy ................ G01N 21/3504
                                                    250/255

\* cited by examiner

OIL-BASED MUD DRILL CUTTING CLEANING FOR INFRARED SPECTROSCOPY

FIELD

The subject disclosure generally relates to the field of infrared spectroscopy analysis of samples from subterranean rock formations. More particularly, the subject disclosure relates to techniques for sample preparation of oil-based mud drill cuttings for infrared spectroscopy characterization of subterranean rock formations.

BACKGROUND

Drill cuttings sample preparation for mud logging typically involves collecting material from a shale shaker into a sieve, rinsing the material with diesel or water, and then with a solvent. The samples can also be baked in an oven or rinsed with soap and water to remove drilling fluid.

Techniques for preparation of drill cuttings for infrared spectroscopy analysis are discussed in U.S. Pat. Appl. Publ. No. 2013/0269933, which is incorporated herein by reference, and referred to hereinafter as "the '933 application." The discussed techniques include: (1) rinsing the cuttings with drilling base-fluid in a sieve (waste base-fluid is disposed); rinsing the cuttings with a solvent in a sieve (waste solvent is disposed); (3) crushing the cuttings to a powder; and (4) exposing the crushed cuttings to a solvent a second time in a vacuum filtration set-up (waste solvent is disposed). In (1) and (2) of the discussed technique the intention is to remove drilling fluid and mud additives from the surface of the cuttings.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to some embodiments, a method is described for recovering hydrocarbons from a formation. The method includes: collecting a formation sample comprising cuttings from a borehole traversing the formation; exposing the sample to a first cleaning fluid at a fluid pressure greater than ambient pressure; crushing and/or grinding the sample cleaned with the first cleaning fluid into particles; analyzing the sample; and characterizing the organic or inorganic content of the formation sample based on the analysis.

According to some embodiments, the sample is exposed to a second cleaning fluid at greater than ambient fluid pressure, thereby removing at least a portion of the first cleaning fluid from the sample. The exposing of the sample to the second cleaning fluid can include vacuum filtration.

According to some embodiments, the sample is exposed to the first cleaning fluid at a fluid pressure of at least 5 psi which can be generated, for example, using a syringe. According to some embodiments, the first cleaning fluid is continuously in contact with the sample, which can be achieved, for example, by placing the sample inside a syringe and drawing the first cleaning fluid into the syringe. The fluid pressure is increased within the syringe using the plunger which also expels the first cleaning fluid from the syringe. According to some other embodiments, the sample is exposed to the first cleaning fluid by expelling the first cleaning fluid from the syringe under pressures of at least 5 psi onto the sample.

The first cleaning fluid can be an oil used as a predominant base oil of drilling mud being used to drill the borehole, and the second cleaning fluid can be a solvent such as: pentane, hexane, heptane, acetone, toluene, benzene, xylene, chloroform or dichloromethane. According to some embodiments, the first cleaning fluid is held in a covered reservoir and reused for several cleaning cycles. The reservoir can have a dome-shaped lid and an opening for the syringe away from the top of the lid, which reduces fumes escaping from the cleaning fluids contained therein.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein.

DETAILED DESCRIPTION

The particulars shown herein are by way of example and for purposes of illustrative discussion of the examples of the subject disclosure only, and are presented in the cause of providing what is believed to be the most useful and readily understood description of the principles and conceptual aspects of the subject disclosure. In this regard, no attempt is made to show more detail than is necessary, the description taken with the drawings making apparent to those skilled in the art how the several forms of the subject disclosure may be embodied in practice. Furthermore, like reference numbers and designations in the various drawings indicate like elements.

According to some embodiments, techniques are described for cleaning oil-based mud cuttings of drilling fluid and mud additives. In some examples, cuttings are placed on a sieve and rinsed with diesel. The rinsed cuttings are put in a syringe, which is alternatively filled and emptied of diesel. The cuttings are left in the syringe, which is then alternatively filled and emptied of pentane. The cuttings are then dried, crushed and exposed to solvent a second time as described in the '933 application. According to some other embodiments, following the initial diesel rinse, the cuttings remain on a sieve and the syringe is used to spray the cuttings with diesel, followed by pentane.

Figure 1:
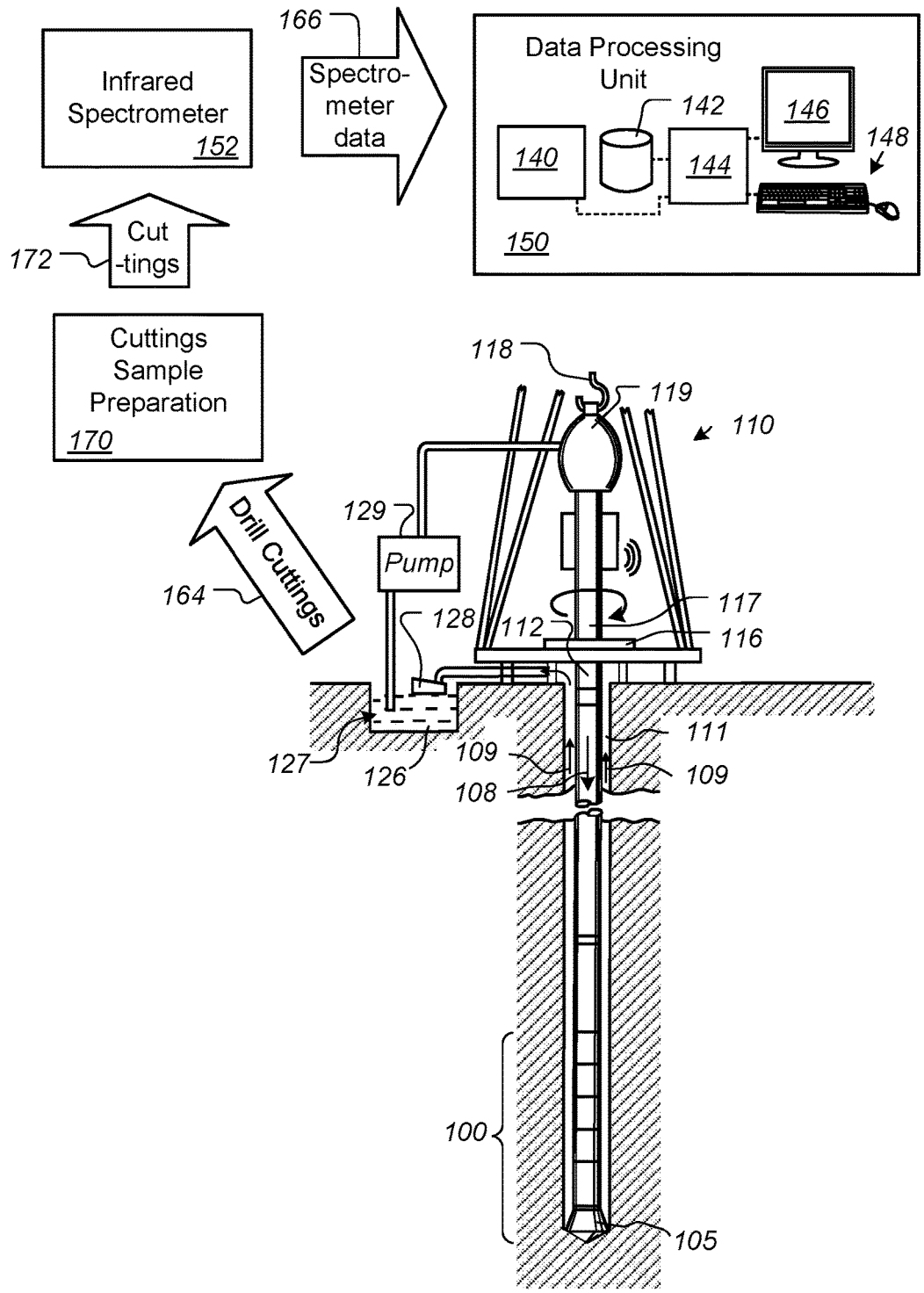
FIG. 1 is a diagram illustrating a wellsite system in which oil-based mud drill cuttings are cleaned for infrared spectrometry analysis, according to some embodiments.

FIG. 1 is a diagram illustrating a wellsite system in which oil-based mud drill cuttings are cleaned for infrared spectrometry analysis, according to some embodiments. The wellsite can be onshore or offshore. In this exemplary system, a borehole 111 is formed in subsurface formations by rotary drilling in a manner that is well known.

A drill string 112 is suspended within the borehole 111 and has a bottom hole assembly 100 that includes a drill bit 105 at its lower end. The surface system includes platform and derrick assembly 110 positioned over the borehole 111, the assembly 110 including a rotary table 116, kelly 117, hook 118 and rotary swivel 119. The drill string 112 is rotated by the rotary table 116, energized by means not shown, which engages the kelly 117 at the upper end of the drill string. The drill string 112 is suspended from a hook 118, attached to a traveling block (also not shown), through the kelly 117 and a rotary swivel 119, which permits rotation of the drill string relative to the hook. As is well known, a top drive system could alternatively be used.

According to some embodiments, the surface system further includes drilling fluid or mud 126, stored in a pit 127 formed at the well site. A shale shaker 128 removes drill cuttings from the mud. A pump 129 delivers the drilling fluid 126 to the interior of the drill string 112 via a port in the swivel 119, causing the drilling fluid to flow downwardly through the drill string 112, as indicated by the directional arrow 108. The drilling fluid exits the drill string 112 via ports in the drill bit 105, and then circulates upwardly through the annulus region between the outside of the drill string and the wall of the borehole, as indicated by the directional arrows 109. In this well-known manner, the drilling fluid lubricates the drill bit 105 and carries formation cuttings up to the surface as it is returned to the shaker 128 and then to pit 127 for recirculation.

According to some embodiments, drill cuttings 164 are taken from the shale shaker 128, and cleaned according to a preparation technique 170 prior to being analyzed using infrared spectrometer 152. According to some embodiments, spectrometer 152 performs Fourier transform infrared spectroscopy (FTIR). According to some embodiments, spectrometer is used to perform transmission FTIR and/or DRIFTS measurements. According to other embodiments, other types of measurements can be made with spectrometer 152, or in place of spectrometer 152. Examples include: other types of infrared spectroscopy; TOC analysis by acidization; Rock Eval pyrolysis; Fischer Assay; XRD; XRF; WDX; EDX; gas sorption; pyconometry; and porosimetry.

The data 166 from the infrared spectrometer 152 is processed by a processing unit 150. Unit 150 can be located in a logging truck or at some other location at the wellsite. According to some embodiments, sample prep 170, spectrometry using IR spectrometer 152 and/or data processing unit 150 are located at one or more locations remote from the wellsite, such as in a remote laboratory. The processing unit 150 preferably includes one or more central processing units 144, storage system 142, communications and input/output modules 140, a user display 146 and a user input system 148. According to some embodiments, the computer programs and hardware shown unit 150 may be distributed across devices including, but not limited to, tooling which is inserted into the borehole and equipment which is located at the surface, whether onsite or elsewhere.

Figure 2:
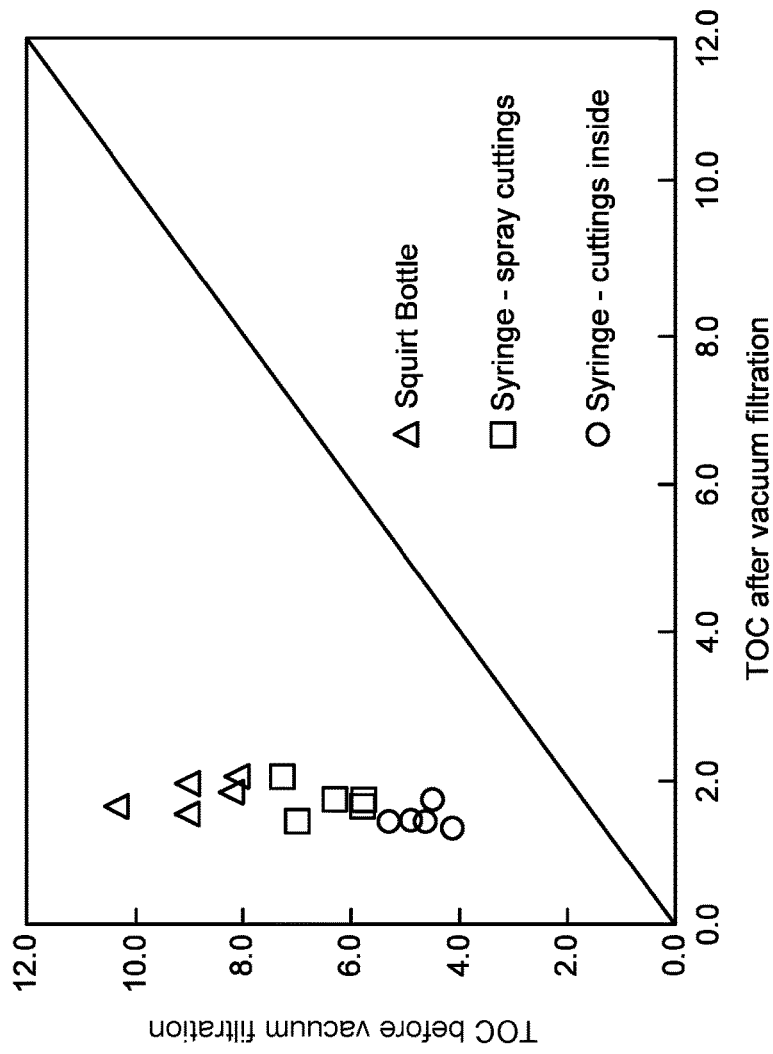
FIG. 2 is a diagram comparing different cuttings cleaning techniques, according to some embodiments.

It has been found that significant concentrations of diesel and/or drilling fluid remain on the cuttings after rinsing in the sieve. FIG. 2 is a diagram comparing different cuttings cleaning techniques, according to some embodiments. In chart 210, total organic carbon (TOC) before and after vacuum filtration is plotted for squirt bottle cleaning (technique used in the '933 application), and for two different pressurized cleaning techniques (inside a syringe and sprayed using a syringe). Chart 210 shows that by cleaning the cuttings using the two described techniques, either inside the syringe or sprayed, more organics are consistently removed from the surface of the cuttings than by spraying in a sieve with a squirt bottle. Since the described cleaning techniques rely less on the thoroughness of the operator in the final cleaning step, more consistent cleaning results are achieved. Furthermore, less pentane will be used to complete the cleaning as the pentane reservoir is preserved for subsequent samples.

Additionally, in the case where the cuttings are loaded into the syringe, the cuttings are put in constant contact with the solvent. Due to this constant, or prolonged, contact, the solvent has time to diffuse into the cuttings and wash out oil-based mud from inside the pore space. While using a squirt bottle to rinse the sample can still remove the oil-based mud from the outside of the cuttings, it is believed that the pore space cannot be accessed. Thus, by loading the cuttings sample inside the syringe this has an added benefit of constant exposure to the cleaning fluid which further enhances cleaning and further decreases variability in cleaning results.

According to some embodiments, the sample preparation of drill cuttings is improved by cleaning them using the described techniques. As can be seen in chart 210, described cleaning techniques more consistently remove the drilling fluid and mud additives from the cuttings surface before the vacuum filtration step. These techniques therefore reduce the variability in cleaning from operator to operator. Furthermore, the waste solvent generated during the vacuum filtration can be reused.

Figure 3:
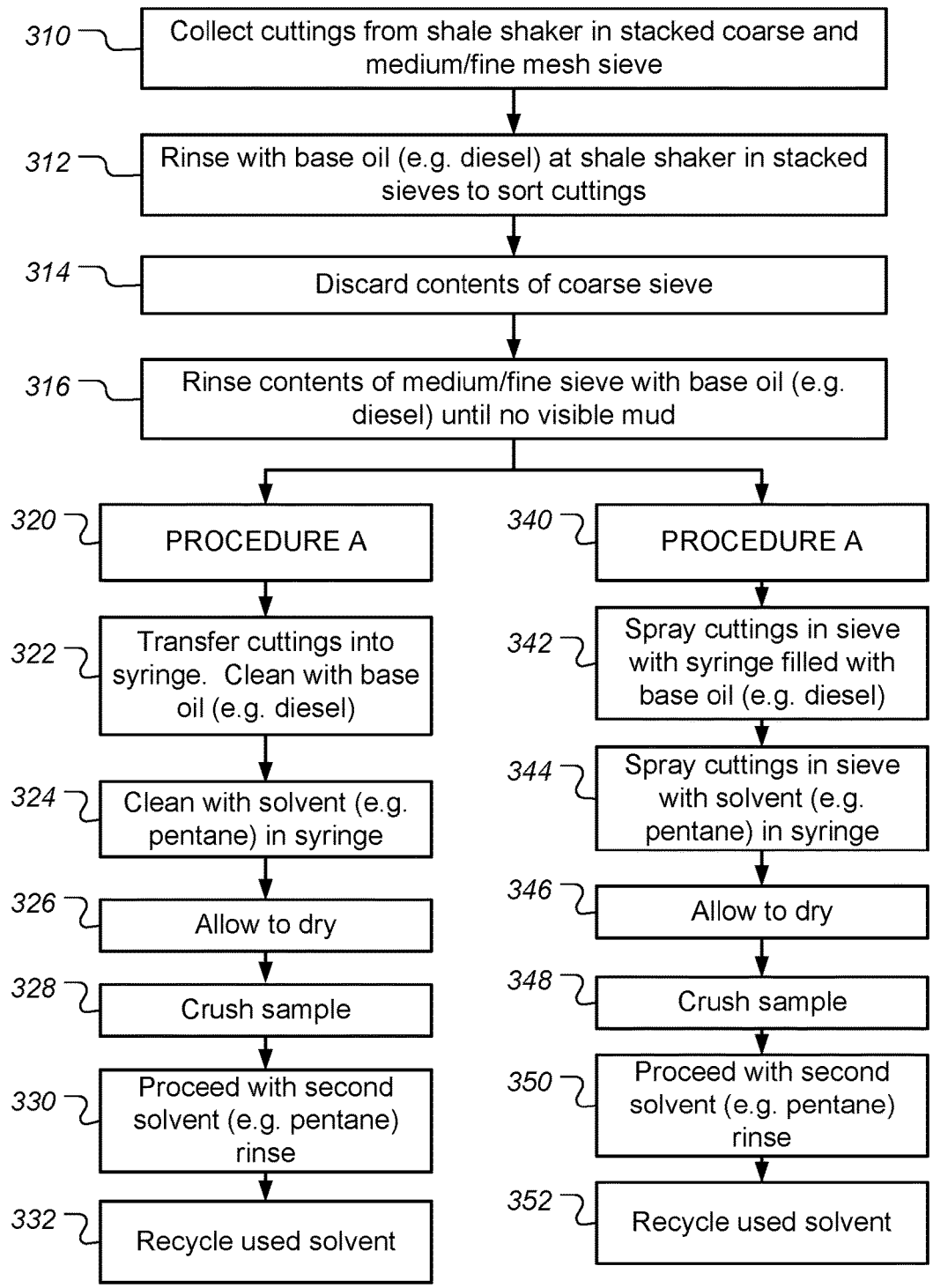
FIG. 3 is a work flow diagram illustrating aspects of drill cuttings cleaning techniques using pressurized fluid, according to some embodiments.

FIG. 3 is a work flow diagram illustrating aspects of drill cuttings cleaning techniques using pressurized fluid, according to some embodiments. The workflow shows cleaning with pressure either inside the syringe, where constant solvent to sample contact can be achieved ("Procedure A") or with pressurized spray ("Procedure B"). The workflow forms part of the cuttings sample preparation block 170 in FIG. 1.

In block 310, drill cuttings are collected from the shale shaker using a sieve that includes stacked coarse and medium/fine mesh. In some examples, to sort the cuttings, the coarse mesh is approximately 5 mm in size and a medium/fine mesh is approximately 1 mm in size. In block 312, the cuttings are rinsed with diesel (or whatever base oil is used in the mud) at the shale shaker in the stacked sieves. The diesel rinsing of block 312 can be performed using various methods such as: diesel from a hose, a diesel sink, a squirt bottle, or by dipping the stacked sieves in a bucket of diesel and agitating.

In block 314, the contents of the coarse sized sieve are discarded, as being likely due to cavings. In block 316, the diesel rinsing is continued until there is no visible mud. For example, pouring diesel over the 1 mm sieve and the agitation is continued until there is no visible mud in the sieve and the diesel runoff is the natural color of the diesel.

Following block 316, two example procedures are outlined: Procedure A (block 320) in which the cuttings are transferred into a syringe (block 322): and Procedure B (block 340) in which a syringe is used to spay the cuttings in a sieve (block 342). In either case, a diesel reservoir (e.g. a 5 gallon bucket) may be used to remove the remaining drilling fluid and mud additives from the cuttings.

In block 322, the cuttings (e.g. >1 mm in size) are transferred to the syringe (e.g. using a spoon). The syringe is filled with a predetermined amount of cuttings (e.g. to the 10 ml line which would be approximately 10 g of cuttings). The remaining cuttings can be discarded. Diesel (or whatever base oil is used in the mud) is then drawn into the syringe and then a predetermined amount (e.g. 50 ml) is pushed out of the syringe at a time until the diesel in the syringe appears to be the natural color of diesel. 150 ml diesel is typically needed to clean the cuttings, but more or less can be used as needed. Clean diesel can be used and discarded as waste for each rinsing cycle, or, to conserve diesel, the same diesel from a reservoir (e.g. 5 gallon bucket) can be used with each rinse. The syringe can have a nozzle that is sized such that particles of interest are too large to pass through it and therefore remain inside the syringe.

In block 342, the cuttings (e.g. >1 mm in size) are left on the sieve. A predetermined amount (e.g. 50 ml) of diesel (or whatever base oil is used in the mud) is drawn into the syringe (or other tool that creates pressurized spray) and the cuttings are flushed with the pressurized diesel. The pressurized spray rinsing is repeated until the diesel runoff appears the natural color of diesel. This is typically 200-250 ml diesel. Clean diesel can be used and discarded as waste for each rinsing cycle, or, to conserve diesel, the same diesel from a reservoir (e.g. 5 gallon bucket) can be used for each rinse. Although diesel is described in blocks 312, 316, 322 and 342 since a typical base oil for the drilling mud is mostly diesel fuel, other fluids can be used depending upon the base oil used in the particular application. For example, oils such as mineral oil, paraffin oil and synthetic oils such as ester and olefin oils, or a combination thereof can be used with or without diesel in blocks 312, 316, 322 and/or 342.

In blocks 324 and 344 pentane is used to remove the diesel from the cuttings. In the case of block 324 the same syringe or a new syringe can be used with the cuttings inside. A predetermined amount (e.g. 50 ml) of pentane is drawn into and then pushed out of the syringe. The process is repeated until pentane in the syringe appears clear. 150 ml pentane is typically needed to clean the cuttings, but more or less can be used as needed. Clean pentane can be used and discarded as waste for each rinsing cycle, or, to conserve pentane, the same pentane from a reservoir (e.g. 5 gallon bucket) can be used with each rinse.

In the case of block 344, where the cuttings were left on the sieve, a predetermined amount (e.g. 50 ml) of pentane is drawn into the syringe (or other tool that creates pressurized spray). The cuttings are then flushed with pressurized pentane. The flushing process is repeated until the pentane runoff appears clear, this is typically 200-250 ml pentane. Clean pentane can be used and discarded as waste for each rinsing cycle, or, to conserve pentane, the same pentane from a reservoir (e.g. 5 gallon bucket) can be used for each rinse. In either case, the cuttings are then allowed to dry (blocks 326 and 346), and the sample is then crushed (blocks 328 and 348).

In blocks 330 and 350 a final vacuum filtration step is carried out as described in the '933 application. Pentane run off from the vacuum flask can be recycled and added to the reservoir to conserve pentane (blocks 332 and 352). According to some embodiments, solvents other than pentane can be used for blocks 324, 344, 330 and/or 350. For example, other common laboratory solvents that may suffice for this application alone or in combination include: hexane, heptane, acetone, toluene, benzene, xylene, chloroform and/or dichloromethane. Furthermore, according to some embodiments, a surfactant (e.g. ethylene glycol or monobutyl) may be added to the solvent for blocks 324, 344, 330 and/or 350. After completing the cleaning technique, the cuttings are sufficiently clean, have the correct particle size and have retained their kerogen and bitumen. They are now ready for analysis of maturity, organic content, mineralogy, surface area, pore volume porosity, etc. by instruments such as FTIR and gas sorption among many others. Additional tests may include transmission FTIR, DRIFTS, other types of infrared spectroscopy, TOC analysis by acidization, Rock Eval, Fischer Assay, XRD, XRF, WDX, EDX, gas sorption, pyconometry, and porosimetry.

Figure 4:
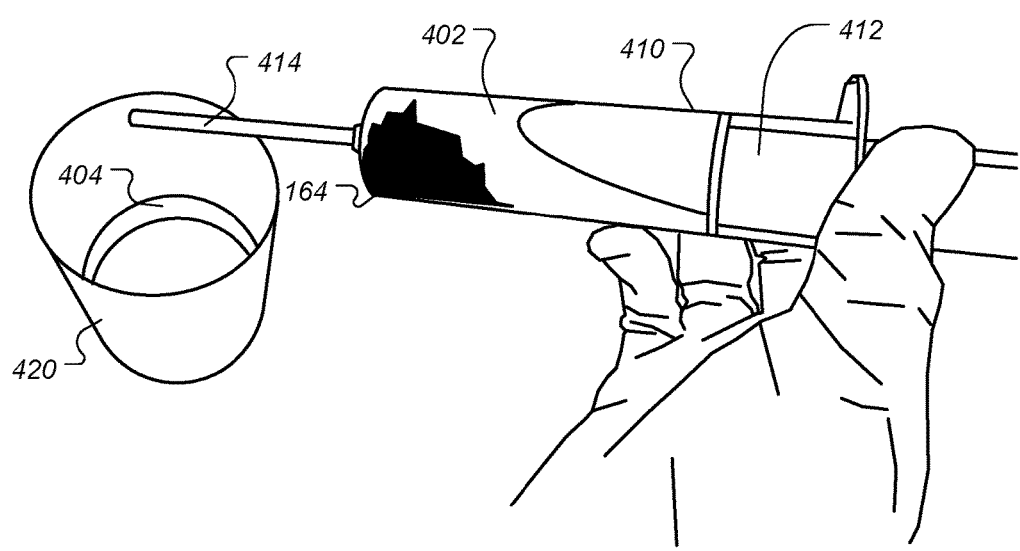
FIG. 4 is a diagram illustrating aspects of a pressurized fluid cuttings cleaning technique according to some embodiments.

FIG. 4 is a diagram illustrating aspects of a pressurized fluid cuttings cleaning technique, according to some embodiments. Shown is the case where the cuttings are put (or left) inside a syringe for pressurized rinsing with pentane, such as in block 324 of FIG. 3. Cuttings 164 are shown inside syringe 410 being rinsed with pentane 404 in container 420. The pentane 402 is drawn into the syringe 410 using plunger 412. Following this, the pentane 402 is then pushed back out of the syringe 410 under pressure from the plunger 412. As described, supra, the rinsing process would be repeated until pentane in the syringe appears clear. Note that the syringe 410 has a nozzle 414 that is sized such that particles of interest of cuttings 164 are too large to pass through it and therefore remain inside the syringe 410.

Figure 5:
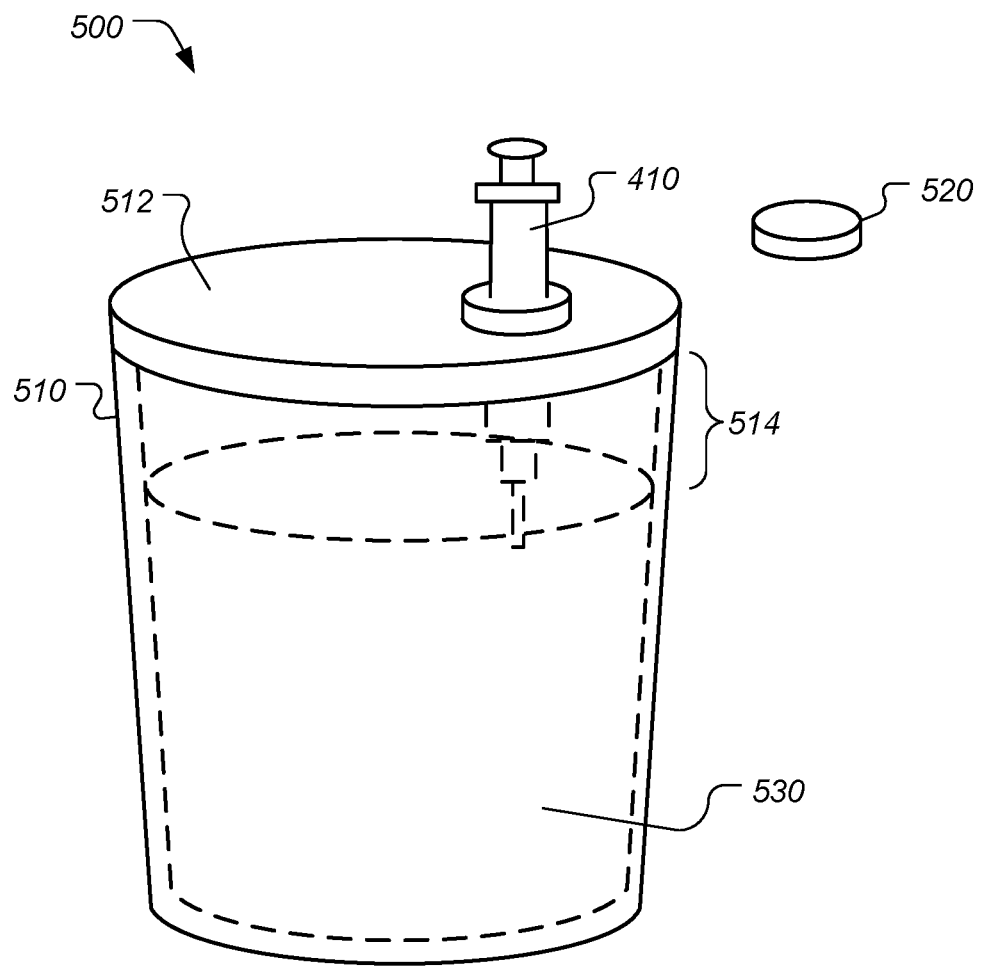
FIGS. 5 and 6 are diagrams illustrating possible set ups for diesel or pentane reservoirs, according to some embodiments.
Figure 6:
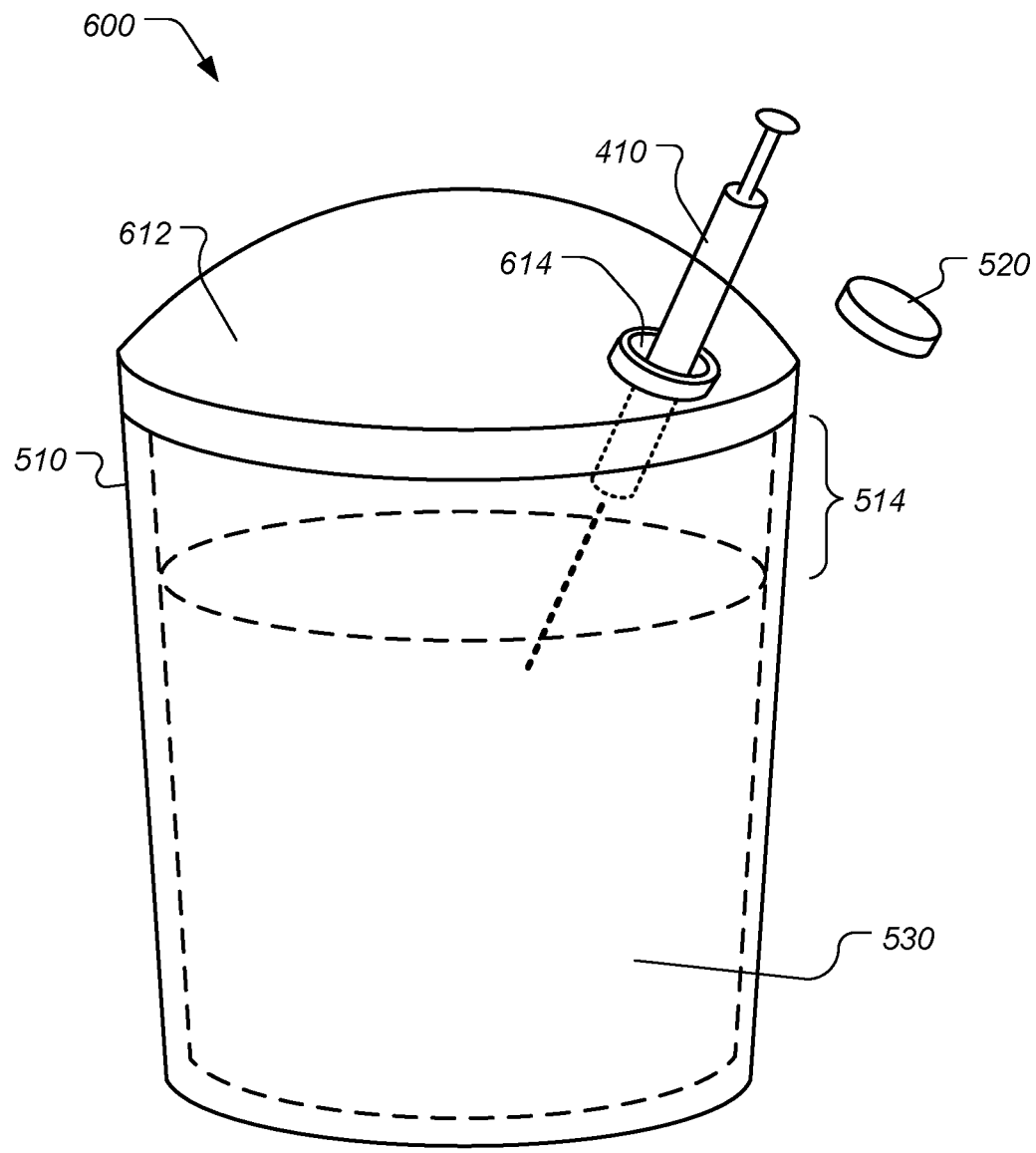

FIGS. 5 and 6 are diagrams illustrating possible set ups for diesel or pentane reservoirs, according to some embodiments. In FIG. 5, the reservoir 500 includes a bucket 510 and a lid 512 that could be flat as shown. Solvent 530 (e.g. diesel or pentane) resides in the bucket 510. The opening for the syringe 410 could be at the top as shown, or on the side. When not in use with a syringe, a cap 520 can be used to seal the syringe opening. Note that the evaporated solvent is trapped in volume 514 and thus stays in the reservoir. In FIG. 6, the reservoir 600 includes a dome-shaped lid 612 with a syringe opening 614 off to one side (away from the top of the dome). Of concern in operating in a closed environment such as a lab is fumes escaping into the environment during the cleaning process. The covered reservoirs 500 and 600 are effective in reducing the escape of such vapors. In the case of the dome-shaped lid arrangement of reservoir 600, where the syringe is operated from the side, the chances of fumes escaping to the closed environment are further reduced since the vapors rise to the top of the lid 612, which is above the location of opening 614.

Although only a few examples have been described in detail above, those skilled in the art will readily appreciate that many modifications are possible in the examples without materially departing from this subject disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method for recovering hydrocarbons from a formation, comprising the steps of:

collecting a formation sample comprising cuttings from a borehole traversing the formation;

exposing the sample to a first cleaning fluid at a fluid pressure;

forming the sample cleaned with the first cleaning fluid into particles, wherein the forming comprises crushing, grinding or a combination thereof;

analyzing the sample;

characterizing an organic or inorganic content of the formation sample based on the analysis; and placing at least a portion of the sample into a syringe and wherein the sample is continuously exposed to the first cleaning fluid by drawing the first cleaning fluid into the syringe while the at least a portion of the sample is within the syringe followed by increasing the fluid pressure within the syringe using a plunger to expel the first cleaning fluid from the syringe.

2. The method of claim 1, further comprising:

exposing the sample to a second cleaning fluid at greater than ambient fluid pressure, thereby removing at least a portion of the first cleaning fluid from the sample.

3. The method of claim 2, wherein the exposing the sample to the second cleaning fluid comprises vacuum filtration.

4. The method of claim 1, wherein the sample is exposed to the first cleaning fluid at a fluid pressure of at least 5 psi.

5. The method of claim 1, wherein the first cleaning fluid is continuously in contact with the sample during said exposing the sample to the first cleaning fluid.

6. The method of claim 1, wherein said exposing the sample to the first cleaning fluid is repeated until the expelled first cleaning fluid appears to be a color of the first cleaning fluid.

7. The method of claim 1, wherein the sample is exposed to the first cleaning fluid by expelling the first cleaning fluid from the syringe at pressures of at least 5 psi onto the sample.

8. The method of claim 1, wherein the first cleaning fluid is an oil.

9. The method of claim 2, wherein the second cleaning fluid is a solvent selected from a group consisting of: pentane, hexane, heptane, acetone, toluene, benzene, xylene, chloroform and dichloromethane.

10. The method of claim 2, wherein the second cleaning fluid is pentane.

11. The method of claim 1 wherein the first cleaning fluid is held in a covered reservoir and reused.

12. The method of claim 11 wherein the covered reservoir comprises a dome-shaped lid and a closable opening through which the syringe can access the first cleaning fluid, the opening being positioned away from a top of the dome-shaped lid.

13. The method of claim 1, further comprising, prior to said exposing, removing particles larger and smaller than a predetermined size range from the sample.

14. The method of claim 1, further comprising:

exposing the grinded or crushed sample to a cleaning fluid.

15. The method of claim 1, wherein the sample is exposed to the first cleaning fluid at a fluid pressure greater than ambient pressure.

* * * * *